United States Patent [19]

Ziemek et al.

[11] 4,089,901

[45] May 16, 1978

[54] PROCESS FOR CONVERTING POLYAMINOPOLYARYL-METHANES INTO DIAMINODIARYLMETHANES

[75] Inventors: Peter Ziemek, Cologne; Roderich Raue, Leverkusen; Hans-Josef Buysch, Krefeld, all of Germany

[73] Assignee: Bayer Aktiengesellschaft, Leverkusen, Germany

[21] Appl. No.: 441,931

[22] Filed: Feb. 12, 1974

[30] Foreign Application Priority Data

Feb. 17, 1973 Germany ............................ 2308014

[51] Int. Cl.$^2$ ............................................. C07C 85/24
[52] U.S. Cl. ........................ 260/570 D; 260/453 AM
[58] Field of Search .................................. 260/570 D

[56] References Cited

U.S. PATENT DOCUMENTS

| 2,511,748 | 6/1950 | Smith et al. .................. 260/570 X |
| 3,362,979 | 1/1968 | Bentley ........................ 260/570 X |

FOREIGN PATENT DOCUMENTS

| 1,127,347 | 9/1968 | United Kingdom ................ 260/570 |
| 1,169,127 | 10/1967 | United Kingdom ................ 260/570 |

*Primary Examiner*—Robert V. Hines
*Attorney, Agent, or Firm*—Gene Harsh; Joseph C. Gil; William E. Parry

[57] ABSTRACT

Polyaminopolyarylmethanes and a monoarylamine are heated in water in the presence of a solid acid catalyst insoluble in the reaction mixture to convert the polyarylaminopolyarylmethanes into diaminodiarylmethanes.

5 Claims, No Drawings

PROCESS FOR CONVERTING POLYAMINOPOLYARYL-METHANES INTO DIAMINODIARYLMETHANES

This invention relates generally to amines and more particularly to a process for preparing a diaminodiarylmethane from a polyaminodiarylmethane.

A process for converting polyaminopolyarylmethanes into diaminodiarylmethanes by heating a mixture of a polyaminopolyarylmethane and a monoarylamine in the presence of solid acid catalysts which are insoluble in the reaction mixture has been disclosed in U.S. patent application Ser. No. 270,918 and now abandoned. The products obtained by the process disclosed in the U.S. patent application are heavily contaminated with by-products which do not contain aromatically bound amino groups. This is a serious disadvantage especially for the preparation of diaminodiphenylmethanes used as the starting materials for the preparation of the corresponding diisocyanates because the by-products are not available for the phosgenation reaction used to produce the corresponding isocyanates but instead give rise to the formation of by-products which are modified by the action of phosgene. These modified by-products have an unpleasant lachrymatory effect and, moreover, rapidly inactivate the activators normally used for the production of polyurethane foams.

It is therefore an object of this invention to provide a process for making diaminodiarylmethanes for polyaminopolyarylmethanes which is devoid of the foregoing disadvantages. Another object of the invention is to provide a process for converting polyaminopolyarylmethanes into diaminodiarylmethanes which are suitable for phosgenation to produce the corresponding diisocyanates.

The foregoing objects and others are accomplished in accordance with this invention, generally speaking, by providing a process wherein polyaminopolyarylmethanes and a monarylamine are heated in water in the presence of a solid acid catalyst which is insoluble in the reaction mixture.

It has been found surprisingly that the disadvantages inherent in the process disclosed in U.S. patent application Ser. No. 270,918 and now abandoned are avoided by heating the polyaminopolyarylmethane and monarylamine in the presence of water. The reaction of polyaminopolyarylmethanes with a monoarylamine in the presence of solid acid substances which are insoluble in the reaction mixture results in exceptionally pure diaminodiarylmethanes if the reaction is carried out in the presence of water. Apparently, the water suppresses the side reactions which give rise to the impurities in the product of the U.S. patent application Ser. No. 270,918 and now abandoned so that the diaminodiarylmethane requires no further purification.

This invention therefore provides a process for the preparation of diaminodiarylmethanes containing a high proportion of 2,4'-diaminodiarylmethane by heating a mixture of polyarylamines of the following general formula

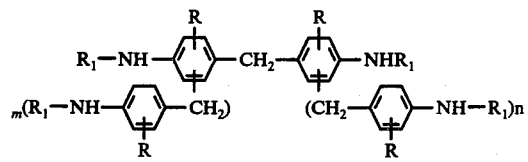

wherein
$n$ represents an integer of from 0 to 2,
$m$ represents an integer of from 0 to 2,
R represents hydrogen, a halogen atom, an alkyl group containing 1 to 4 carbon atoms, an alkoxy group containing 1 to 4 carbon atoms, an aralkyl group containing 7 to 10 carbon atoms or a condensed benzene ring and
$R_1$ represents hydrogen or an alkyl group containing 1 to 4 carbon atoms
with a monoarylamine of the general formula

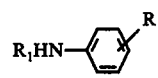

wherein
R and $R_1$ have the meanings indicated above in the presence of a solid acid catalyst which is insoluble in the reaction medium, characterized in that the reaction is carried out in the presence of water.

By substances which are acid in reaction are meant substances which can be titrated with potassium hydroxide in an aqueous medium including those described in U.S. patent application Ser. No. 270,918.

The general formula for polyarylamines shown above represents the mixture normally obtained by the known process of arylamine/formaldehyde condensation, the individual components of which conform substantially to this general formula. The polyarylamine mixtures used as the starting material are prepared in known manner by the condensation of aromatic amines with formaldehyde in the presence of equimolecular quantities or smaller quantities or even only catalytic quantities of inorganic or organic acids such as hydrochloric acid, sulphuric acid, phosphoric acid, acetic acid or the like. The condensation of aromatic amines with formaldehyde may also be carried out according to another known method at an elevated temperature in the presence of catalytic quantities of acid and inorganic salts such as sodium chloride or in the presence of carbon dioxide. The mixture obtained contains either a higher proportion of diaminodiarylmethanes or a higher proportion of polyaminopolyarylmethanes, depending on the molar ratio of arylamine/formaldehyde employed. Any of these mixtures are suitable starting materials for the process according to the invention. Diaminodiarylmethane compounds separated from the mixture by distillation or polyaminopolyarylmethanes which remain behind as a distillation residue and contain only small quantities of diaminodiarylmethane compounds are also suitable.

The amines used as starting materials for the process of condensation with formaldehyde to prepare the polyaminopolyarylmethanes used according to the invention may be any arylamines of the general formula

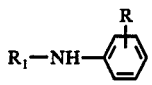

in which
- R represents hydrogen, a halogen atom, an alkyl group containing 1 to 4 carbon atoms, an alkoxy group containing 1 to 4 carbon atoms, an aralkyl group containing 7 to 10 carbon atoms or a condensed benzene ring and
- $R_1$ represents hydrogen or an alkyl group containing 1 to 4 carbon atoms.

The following are examples of suitable amines for condensation with formaldehyde: aniline, o-chloroaniline, m-chloroaniline, p-chloroaniline, o-bromoaniline, m-bromoaniline, p-bromoaniline, o-anisidine, m-anisidine, p-anisidine, o-phenetidine, m-phenetidine, p-phenetidine, o-toluidine, m-toluidine, p-toluidine, 2-ethylaniline, 2-isopropylaniline, 2,6-diethylaniline, N-methylaniline, N-ethylaniline, N-propylaniline, o-benzylaniline, m-benzylaniline, p-benzylaniline, α-naphthylamine and the like. Aniline is preferred.

The polyaminopolyarylmethane mixtures used for the process according to the invention preferably contain up to 10% by weight of dinuclear, 20 to 60 percent by weight of trinuclear, 20 to 45 percent by weight of tetranuclear and 5 to 20 percent by weight of higher nuclear polyaminopolyarylmethanes. In a special method of carrying out the process of the invention, however, a diaminodiarylmethane mixture consisting predominantly of 4,4'-isomers may be used as starting material a considerable proportion of the 4,4'-isomer being converted into the corresponding 2,4'-isomer. This special variation of the process according to the invention therefore does not serve to convert polyaminopolyarylmethanes having more than two arylamino groupings into diaminodiarylmethanes but merely to convert 4,4'-isomers into 2,4'-isomers.

The aromatic monoamines used in mixtures with the polyaminopolyarylmethanes which have been obtained by amineformaldehyde condensation may be any amines of the general formula

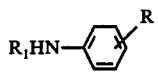

in which R and $R_1$ have the meanings indicated above. The amines mentioned above are suitable examples. Aniline is also in this case the preferred amine to be used.

The process according to the invention is carried out using solutions of the polyamine in the aromatic monoamine to which are added between 5 and 200 percent by weight, preferably 10 – 50 percent by weight, of water, based on the total quantity of mixture.

The proportion by weight of polyamine is monoamine is not critical and may be between 1 : 1 and 1 : 20 but may also be above or below these limits. The greater the excess of monoamine used, the greater is the proportion of polyaminopolyphenylmethanes converted into diaminodiphenylmethanes.

The catalysts used in the process according to the invention may be any substance which is acid in reaction and completely insoluble in the amines used and which has a higher melting point than the temperature employed in the process according to the invention. Suitable catalysts are, for example, silicic acid/alumina gels such as montmorillonites and zeolites, fuller's earth, bauxite, bentonite or kieselguhr, any of which may, if indicated, be treated with acid before use. Aluminum oxides, boron phosphates and tin phosphates are also suitable, and oxides of iron, chromium, titanium or zirconium may be added to them. If the process according to the invention is carried out discontinuously, the catalyst may be used in an amount of 1 to 50 percent by weight, preferably 5 to 20 percent by weight, based on the quantity of polyaminopolyarylmethane used. The catalyst may be recovered after the reaction by filtration and used for another batch of reaction mixture. It is particularly advantageous, however, to carry out the process continuously, in which case the catalyst may be arranged as a stationary phase in a solid bed, for example in the form of pellets, small cylinders or tablets.

The process according to the invention may be carried out at temperatures of 150° to 400° C, preferably 250° to 350° C. The reaction time in the discontinuous process or average time of stay in the continuous process depends largely on the nature of the catalyst and the reaction temperature. It is generally between one minute and 24 hours, in most cases between 5 and 300 minutes.

If the discontinuous method is employed, the process according to the invention is advantageously carried out in a conventional autoclave. The catalyst may be removed by filtration after the reaction and used for another batch of reaction mixture. The process is, however, preferably carried out continuously. In that case, the catalyst is arranged, e.g. in a pressure tube heated to the reaction temperature and the mixture of polyaminopolyarylamine and monoarylamine and water is run over the catalyst, the reaction pressure becoming established at the vapor pressure of the mixture of monoarylamine and water. The amine mixture may be passed through the reaction tube either from above, downwards or from below upwards. When the reaction has terminated, unreacted monoarylamine is first distilled off and, if desired, the polyamine mixture obtained is then processed by distillation. Any of the usual methods of separation may be employed for isolating the diaminodiarylmethanes obtained by the process according to the invention. It is particularly advantageous to employ a method of thin layer distillation because this has the least harmful effect on the mixture of higher nuclear homologs remaining behind, which can then be returned to the process. Alternatively, aniline may first be driven out of the reaction product in a distillation column by means of superheated steam, the amine mixture remaining behind being thereafter separated into diaminodiarylmethane compounds and polyaminopolyacrylmethanes by thin layer distillation.

As already mentioned above, the process according to the invention may be employed for preparing diaminodiarylmethanes with a high proportion of 2,4'-isomers. The proportion of 2,4'-diaminodiarylmethane in the mixture of diaminodiarylmethane isomers obtainable by the process according to the invention is generally between 40% and 70%.

The process according to the invention is of particular technological interest for the production of mixtures of diaminodiphenylmethane isomers with a high proportion of 2,4'-diaminodiphenylmethane by the reaction of polyaminopolyphenylmethanes with aniline according to the invention because such isomeric diaminodiphenylmethane mixtures can be converted into extremely valuable diisocyanate mixtures by phosgenation. These isomeric diisocyanatodiphenylmethane mixtures which contain a high proportion of 2,4'-isomers are characterized by their low tendency to crystallization compared with that of 4,4'-diisocyanatodiphenylmethane which crystallizes readily. The amines obtainable by the process according to the invention are also suitable for the preparation of polyureas or for use as hardeners for epoxy resins.

EXAMPLES 1 – 17

240 g of polyaminopolyphenylmethanes containing less than 1 percent by weight of diaminodiphenylmethane are dissolved in 580 g of aniline. X g of water and 17.8 g of silica-alumina LA-3P (Ketjen, Amsterdam, 13.5% of active $Al_2O_3$, 0.03% of $Na_2O$, 0.47% of $SO_4$, 0.03% of Fe and 83% of silicon oxide) are added to this solution. The mixture is heated to Z° C for y minutes in an autoclave.

After removal of the solvent by distillation, a polyamine mixture consisting of A percent by weight of unwanted by-products, B percent by weight of diaminodiphenylmethanes and C percent by weight of higher polyamines is obtained.

The by-products generally have a boiling point intermediate between that of aniline and the boiling point of 2,2'-diaminodiphenylmethane. Quantitative determination of the individual components is carried out by gas chromatography.

EXAMPLES 1 – 17 is pumped at the rate of 1.5 liters per hour per liter of catalyst through a reactor which is filled with solid $SiO_2/Al_2O_3$ catalyst (silica-alumina LA-3P) and which is heated to an operating temperature of 300° C. The operating pressure which becomes established in the reactor is about 60 excess atmospheres. After release of the pressure from the reaction mixture, water and aniline are distilled off and the polyamine obtained is analyzed by gas chromatography and found to have the following composition:

| Unwanted by-products | = 1.1 percent by weight |
|---|---|
| 2,2" | = 4.8 percent by weight |
| 2,4" | = 38.5 percent by weight |
| 4,4" | = 19.7 percent by weight |
| polyamine | = 35.9 percent by weight |

For comparison, a similar experiment carried out without the addition of water yields the following results:

| Unwanted by-products | = 7.8 percent by weight |
|---|---|
| 2,2" | = 11.4 percent by weight |
| 2,4" | = 33.4 percent by weight |
| 4,4" | = 13.5 percent by weight |
| polyamine | = 33.9 percent by weight |

EXAMPLES 20 – 23

240 g of polyaminopolyphenylmethanes containing less than 1 percent by weight of diaminodiphenylmethanes are dissolved in 580 g of aniline, and 100 g of

| Catalyst Example No. | Xg of $H_2O$ | Reaction time y in minutes | Temperature in ° C(2) | Unwanted by-products | B % of diaminodiphenyl-methanes | | | C% of higher polyamines |
|---|---|---|---|---|---|---|---|---|
| | | | | | 2,2' | 2,4' | 4,4' | |
| 17.8 g silica-alumina LA-3P | — | 300 | 300 | 9.1 | 10.2 | 27.1 | 11.0 | 42.6 |
| " | 50 | 300 | 300 | 5.3 | 7.5 | 34.1 | 14.6 | 38.5 |
| " | 100 | 300 | 300 | 3.8 | 5.3 | 35.1 | 15.8 | 40.0 |
| " | 150 | 300 | 300 | 2.8 | 5.8 | 33.4 | 17.8 | 35.2 |
| " | — | 180 | 270 | 2.0 | 9.0 | 42.0 | 18.7 | 28.3 |
| " | 50 | 180 | 270 | 0.5 | 3.8 | 38.0 | 19.0 | 42.7 |
| " | 150 | 180 | 270 | 0.6 | 3.5 | 41.8 | 23.6 | 30.5 |
| " | — | 180 | 250 | 0.4 | 4.8 | 40.5 | 21.3 | 33 |
| " | 50 | 180 | 250 | — | 1.8 | 31.0 | 23.6 | 43.6 |
| " | 100 | 180 | 250 | — | 1.0 | 23.4 | 22.6 | 53.0 |
| " | — | 30 | 300 | 6.2 | 11.3 | 35.6 | 14.4 | 38.7 |
| " | 50 | 30 | 300 | 1.0 | 5.3 | 36.6 | 16.9 | 41.2 |
| " | 150 | 30 | 300 | 0.3 | 3.8 | 38.5 | 21.9 | 35.8 |
| " | — | 30 | 270 | 0.2 | 4.7 | 40.1 | 22.5 | 32.7 |
| " | 50 | 30 | 270 | 0.1 | 1.9 | 24.8 | 17.0 | 56.3 |
| " | 100 | 30 | 270 | 0.1 | 1.7 | 28.1 | 24.1 | 46.1 |
| " | 150 | 30 | 270 | — | 1.4 | 24.0 | 20.1 | 54.5 |

EXAMPLES 18 – 19

A vigorously stirred mixture consisting of
100 parts by weight of water,
580 parts by weight of aniline and
240 parts by weight of polyamine which contains less than 1 percent by weight of diaminodiphenylmethanes water are added. This mixture is stirred in an autoclave with 17.8 g of a catalyst K at 250° C for 3 hours.

After removal of the solvent by distillation, a polyamine mixture consisting of A percent by weight of unwanted by-products, B percent by weight of diaminodiphenylmethanes and C percent by weight of higher polyamines is obtained.

EXAMPLES 20 – 23

| Catalysts K | Unwanted by-products A % | B % of diaminodiphenylmethane | | | Polyamines C % |
|---|---|---|---|---|---|
| | | 2,3 | 2,4 | 4,4 | |
| $Al_2O_3$ activated with 10% $H_2SiF_6$ | 0 | 0.34 | 9.40 | 10.6 | 79% |
| Zeolite X (26% $SE_2O_3$, 1.5% $Na_2O$ 40% $SiO_2$, 30% $Al_2O_3$, | 0.5 | 5.0 | 31.7 | 14.2 | 49.1% |

-continued

| Catalysts K | Unwanted by-products A % | B % of diaminodiphenylmethane | | | Polyamines C % |
| --- | --- | --- | --- | --- | --- |
| | | 2,3 | 2,4 | 4,4 | |
| 3% lost by ignition) Zeolite y (20% SE$_2$O$_3$, 2.5% Na$_2$O 51% SiO$_2$, 24% Al$_2$O$_3$ 2.5% lost by ignition) | 0.3 | 3.8 | 30.7 | 15.8 | 49.7% |
| Decationised zeolite y (63% SiO$_2$, 30% Al$_2$O$_3$, 3.9% Na$_2$O, 4.0% lost by ignition) | 0.3 | 3.9 | 29.8 | 15.4 | 50.9% |

What is claimed is:

1. A process for the preparation of diaminodiarylmethanes containing 2,4'-diaminodiarylmethanes which comprises heating a mixture of a polyarylamine of the general formula

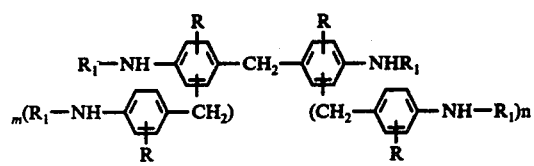

in which n represents an integer of from 0 to 2, m represents an integer of from 0 to 2, R represents hydrogen, a halogen atom, an alkyl group containing 1 to 4 carbon atoms, an alkoxy group containing 1 to 4 carbon atoms, an aralkyl group containing 7 to 10 carbon atoms or a condensed benzene ring, and R$_1$ represents hydrogen or an alkyl group containing 1 to 4 carbon atoms with a monoarylamine of the general formula

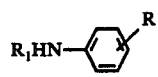

in which

R and R$_1$ have the meanings indicated above and water in the presence of a solid acid catalyst which is insoluble in the reaction mixture.

2. The process of claim 1, wherein the heating is carried out continuously by passing the mixture of amines and water through the catalyst which is arranged as a stationary phase and heated to the reaction temperature.

3. In the preparation of a diaminodiarylmethane by a process wherein a mixture containing a polyaminopolyarylmethane having more than two arylamino groupings and a monoarylamine are heated in the presence of a solid acidic catalyst which is insoluble in the mixture, the improvement which improves the yield of 2,4'-diaminodiarylmethane comprising including water in the said mixture.

4. The process for converting 4,4'-diphenylmethane diamine into 2,4'-diphenylmethane diamine which comprises heating the 4,4'-isomer with an aromatic monoamine in water with a solid acidic catalyst.

5. The process of claim 1 wherein the catalyst is a silica-alumina gel.

* * * * *